(12) United States Patent
Gross

(10) Patent No.: US 8,498,461 B2
(45) Date of Patent: Jul. 30, 2013

(54) METHOD AND MAGNETIC RESONANCE SYSTEM TO DETERMINE SYSTEM-DEPENDENT PHASE INFORMATION

(75) Inventor: Patrick Gross, Langensendelbach (DE)

(73) Assignee: Siemens Aktiengesellschaft, Munich (DE)

( * ) Notice: Subject to any disclaimer, the term of this patent is extended or adjusted under 35 U.S.C. 154(b) by 75 days.

(21) Appl. No.: 13/303,430

(22) Filed: Nov. 23, 2011

(65) Prior Publication Data

US 2012/0134565 A1    May 31, 2012

(30) Foreign Application Priority Data

Nov. 25, 2010   (DE) .......................... 10 2010 061 970

(51) Int. Cl.
    *G06K 9/00*    (2006.01)
    *A61B 5/00*    (2006.01)

(52) U.S. Cl.
    USPC ............................. 382/128; 378/1; 600/410

(58) Field of Classification Search
    None
    See application file for complete search history.

(56) References Cited

U.S. PATENT DOCUMENTS

| | | | | |
|---|---|---|---|---|
| 4,683,431 A * | 7/1987 | Pattany et al. | ................. | 324/306 |
| 4,720,678 A * | 1/1988 | Glover et al. | ................. | 324/309 |
| 5,546,472 A * | 8/1996 | Levin | ............................ | 382/131 |
| 5,759,152 A * | 6/1998 | Felmlee et al. | ................ | 600/410 |
| 5,850,486 A * | 12/1998 | Maas et al. | ..................... | 382/294 |
| 5,903,664 A * | 5/1999 | Hartley et al. | ................. | 382/154 |
| 6,178,271 B1 * | 1/2001 | Maas, III | ....................... | 382/294 |
| 6,192,263 B1 * | 2/2001 | Ma | ................................. | 600/410 |
| 6,249,595 B1 * | 6/2001 | Foxall et al. | ................... | 382/128 |
| 6,321,107 B1 * | 11/2001 | Derbyshire | ................... | 600/410 |
| 6,408,043 B1 * | 6/2002 | Hu et al. | ........................... | 378/8 |
| 6,510,337 B1 * | 1/2003 | Heuscher et al. | ............ | 600/428 |
| 6,603,990 B2 * | 8/2003 | Zhang et al. | ................... | 600/410 |
| 6,714,807 B2 * | 3/2004 | Zur | ................................ | 600/410 |
| 6,937,696 B1 * | 8/2005 | Mostafavi | ....................... | 378/95 |
| 6,985,625 B1 * | 1/2006 | Silver et al. | .................... | 382/195 |
| 7,444,011 B2 * | 10/2008 | Pan et al. | ........................ | 382/131 |
| 7,502,526 B2 * | 3/2009 | Mitchell et al. | ................ | 382/280 |
| 7,561,658 B2 * | 7/2009 | Hempel et al. | ..................... | 378/4 |
| 7,620,444 B2 * | 11/2009 | Le et al. | ......................... | 600/428 |
| 7,835,500 B2 * | 11/2010 | Fu et al. | ......................... | 378/128 |
| 2001/0031037 A1 * | 10/2001 | Prince et al. | ................... | 378/137 |

OTHER PUBLICATIONS

"Referenceless MR Thermometry for Monitoring Thermal Ablation in the Prostate,"Rieke et al., IEEE Trans. on Medical Imaging, vol. 26, No. 6 (2007) pp. 813-821.

"Information Theory, Inference, and Learning Algorithms," MacKay, Section 46.3 (2003) pp. 542-543.

(Continued)

*Primary Examiner* — Manav Seth
(74) *Attorney, Agent, or Firm* — Schiff Hardin LLP

(57) ABSTRACT

In a method to determine an MR system-dependent phase information of a phase value in an MR phase image data set, initial variances are associated with image points of a first phase image data set, and for an additional phase image data set, a phase value and a variance of the phase value for the image points of the additional phase image data set are estimated by a linear transformation of the first phase image data set. The additional image data set is calculated by weighted addition of the phase values of the first phase image data set with the estimated phase values, with the weighting of the two phase values taking place in the addition dependent on the variance belonging to the respective phase value.

14 Claims, 2 Drawing Sheets

OTHER PUBLICATIONS

"Reweighted C1 Referenceless PRF Shift Thermometry," Grissom et al., Magnetic Resonance in Medicine, vol. 64 (2010) pp. 1066-1077.

"An Internal Reference Model-Based PRF Temperature Mapping Method With Cramer-Rao Lower Bound Noise Performance Analysis," Li et al., Magnetic Resonance in Medicine, vol. 62 (2009), pp. 1251-1260.

"Variances in Referenceless Phase Mapping," Gross, (2009), pp. 1-9.

* cited by examiner

METHOD AND MAGNETIC RESONANCE SYSTEM TO DETERMINE SYSTEM-DEPENDENT PHASE INFORMATION

BACKGROUND OF THE INVENTION

1. Field of the Invention

The present invention concerns a method to determine an MR system-dependent phase information of a phase value in an MR phase image data set, and an MR system with which the MR system-dependent phase information can be calculated.

2. Description of the Prior Art

Phase imaging has a broad field of application in magnetic resonance tomography (MRT). For example, the phase information contained in the MR signal can be used in susceptibility-weighted MRT, phase contrast MRT, for flow measurement, to determine the fat content in a tissue, and for thermometry. In thermometry or thermotherapy methods, the temperature in tumor cells is specifically increased in order to kill the cells or to make the tumor cells sensitive to accompanying therapy measures such as chemotherapy or radiation therapy. For example, tissue heating can take place via lasers or ultrasound, or RF antennas. In order to not significantly stress the healthy tissue due to the increased temperature, a temperature monitoring of the heated tissue is required. Due to the temperature dependency of some MR parameters such as the chemical shift, MRT has the potential to non-invasively show temperature changes. Given temperature monitoring based on the temperature dependency of the chemical shift, the resonance frequency altered by the temperature increase is detected in a modified phase position in the image point. However, since the temperature dependency is slight, with $-0.01$ ppm/° C., it is important to know the phase information dependent on the MR system or, respectively, the phase change dependent on the MR system so that the temperature information determined from the phase information is not adulterated. Given temperature imaging based on the chemical shift, only temperature changes can be shown via calculations of phase changes. It is also important to separate the system-induced phase change from the temperature-induced phase change. The phase drift existing over time due to the change of the B0 field can be determined via reference image points that are not heated, for example. Given this difference calculation of phase data sets acquired at different points in time, it can occur that the patient moves or the magnetic environment changes between the measurements.

One problem given the use of phase information is the presence of water and fat molecules in a tissue. First, the resonance frequency of fat and water differ by approximately 3.5 ppm, and second, the chemical shift of fat is not temperature-dependent. In a method named for Dixon, the phase drift generated due to B0 field inhomogeneities is estimated in order to separate fat from water. The standard assumption in Dixon fat-water separation is that the signal in a voxel is generated by two different populations: fat molecules and water molecules. If the fat proportion is designated as r, the water proportion is (1−r), wherein r is between 0 and 1. Each molecule has its own angular frequency $\omega_{fat}$ for fat and $\omega_{water}$ for water. Due to the different resonance frequency, the signal proportions of the two molecules are either in phase or counter-phase depending on the echo time.

Furthermore, techniques known as reference-less methods for generation of phase image data sets are known in which the system-dependent phase information is not measured in an additional reference subject.

For example, in methods with reference subjects the reference subject can be the patient himself, wherein a reference data set is measured before heating. In flow measurement a flow-coding gradient can be activated and deactivated. Flow measurements are often measured without reference subject. Given these reference-less approaches it is assumed that the MR system-dependent phase information changes only slowly over the field of view of the image, such that—if a reliable phase information is known at some image points—the MR system-dependent phase change can be approximated via interpolation, for example via a low order polynomial. However, the selection of valid phase reference points is necessary for this, based on which the phase development across the image can be approximated. It is thus necessary to differentiate between valid image points and other image points in which the MR system-dependent phase influence must be estimated.

This division into valid and invalid image points is difficult to implement since image points must be found in which the tissue is not heated, nor does a possible fat-water combination adulterate the phase information.

SUMMARY OF THE INVENTION

An object of the present invention is to provide a method with which it is possible to determine a spatial, MR system-dependent phase change or, respectively, phase information in an MR phase image data set.

According to a first aspect of the invention, in a method to determine an MR system-dependent phase information of a phase value in an MR phase image data set, in a first step of the invention initial variances are associated with the individual image points of a first phase image data set. This means that initial variances are determined at optimally many image points in a shown examination region. In a further step, to generate an additional phase image data set, a phase value and a variance of the phase value for the image points of the further phase image data set are estimated by subjecting the first phase image data set to a linear transformation and the additional phase image data set is subsequently calculated by weighted addition of the phase values of the first phase image data set with the estimated phase values. The weighting of the two phase values takes place in the addition depending on the variance belonging to the respective phase value. Due to the linear transformation, the phase information in the image points of the first phase image data set is transferred to the phase values of the further image data set. However, the items of phase information contained in the individual image points themselves have a defined uncertainty or imprecision that is expressed by the variance. Given the calculation of the additional image data set or, respectively, given the calculation of the phase values of the additional image data set, the phase information of the first image data set and the phase information of the additional phase image data set are now weighted depending on the variance that is present in the respective image point.

The weighting of a phase value in the addition is preferably higher the smaller the variance belonging to the phase value. Conversely, the weighting of a phase value in the addition is smaller if the associated variance of the phase value is high. Expressed in a different way, phase information in which the phase value can be determined with high precision has a high weighting while phase values in which a precise statement about the phase information is not possible have a low weighting. Instead of the selection of reference image points with which a certain phase position can be associated, and extrapolation of the phase information at the image points for which no certain phase information is present, the image points are accounted for according to the invention depending on their imprecision or variance.

According to a preferred embodiment of the invention, given the association of initial variances the first phase image data set has a first group of image points at which the variance essentially depends on a signal-to-noise ratio of the MR signal with which the first phase image data set was generated. The signal strength—i.e. the magnitude signal—can thereby be considered in relation to the noise. Furthermore, a second group of image points is advantageously provided in which the variance is determined with the aid of a model that is based on the respective image point and with whose help a variance in the image point is determined. As is explained in detail below, the variance of the image points of the second group can be determined, for example, with the use of a model that accounts for which image points are heated, what the fat/water ratio in an image point is, how the susceptibility of the tissue at the image point behaves etc.

The variance-dependent addition and the calculation of the additional phase image data set are repeated iteratively via addition of the phase values of one phase image data set in the iteration step i per −1 and the phase values of the phase image data set at iteration step i. This iteration can be repeated up to the creation of a final phase image data set that then corresponds to the MR system-dependent spatial phase information. In the iteration steps the phase image data sets are subjected to the linear transformation until they approach a final spatial phase distribution across the image, which then corresponds to the system-dependent phase information or, respectively, phase development. If the difference in the phase image data sets between two iteration steps is less than a predetermined limit value, this final image data set is achieved.

The linear transformation can take place by aliasing of the first phase image data set with a filter kernel. Given filtering with a filter kernel, a kernel matrix is applied to each image point of the image, wherein the kernel includes multiplication factors that are applied to the image point itself and its neighbors. The sum of the products of the image point values then replaces the value in an image point with the corresponding matrix elements. An example of a filter kernel is, for example, a three-by-three matrix with zeroes in the diagonal elements and with values of one-quarter in the remaining four matrix elements. Four different filter kernels are naturally possible that form a linear transformation.

It is likewise possible that the additional phase image data set is estimated via aliasing with multiple different filter kernels and the associated variances, wherein the phase values resulting via the aliasing with the filter kernels can respectively be weighted in the addition depending on the associated variance. In particular in cases in which it is not clear which filter kernel should be used, it is possible to apply different filter kernels and to weight the results depending on the associated variance. Since it can be difficult to determine in advance which type of filter kernel should be used—for example whether it should be an interpolating filter kernel or an extrapolating filter kernel—this embodiment with the use of multiple filter kernels offers the advantage to use the different filter kernels and to weight the results depending on their variances. The initial variances are independent of the kernels that are used. However, different linear transformations combine these phases differently, and different variances then also produce the respective (aliased, for example) results. For example, it can be that a filter kernel uses a point with a very high variance (or an invalid image point); the result is then negatively weighted, which is indicated by a high result variance.

A few exemplary embodiments of how initial variances in image points can be associated are explained in the following. In the event that only water molecules and no fat molecules are contained in an image point, here the phase variance in this image point depends on the magnitude of the signal or, respectively, the signal-to-noise ratio of the signal. For this reason the variance in the phase data can vary from image point to image point.

Only a measurement of the phases is typically present, such that no variance can be directly surveyed from the data in statistical methods. The approach sought here is based on the knowledge of the signal-to-noise ratio of the image point. The amplitude of the signal is the magnitude. The noise can be estimated based on multiple methods. Some of these methods are based on the fact that, in the ideal case, the noise in complex MR data has the same Gaussian statistics for all image points. It can thus be estimated particularly well in regions without signal, i.e. in the background or in homogeneous areas. As an alternative to this, a noise measurement can be made in that the signal is measured without excitation pulse, for example. Since the noise response changes in a predictable manner between measurements, for example due to the bandwidth or the k-space scanning, noise measurements do not need to be repeated constantly. The spatial modulation of the variances can also be predicted given parallel acquisition acceleration and incomplete k-space scanning. If a phase is calculated via a logarithm from an MR signal (x) with Gaussian noise and a covariance matrix "C", this calculated phase has a (Laplace-approximated) covariance "D" whose inverse is calculated from the following matrix elements:

$$[D^{-1}]_{nm}=(x_n x_n^*[C^{-1}]_{nm}+x_m^* x_n[C^{-1}]_{mn})/2$$

In the case of a spatially (or spectrally) independent noise distribution (white, Gaussian noise), the matrices "C" and "D" are distorted diagonally and by the following formula:

$$[D^{-1}]_{nn}=x_n x_n^*[C^{-1}]_{nn}$$

The signal dependency of the variance can also be used in image points in which adipose tissue is contained in the image points; however, the adipose signal portion has been suppressed via fat suppression or has been determined with the aid of the Dixon method.

If an image point predominantly contains fat tissue, the initial variance can, for example, be determined with consideration of the fat-induced phase angle and the measured phase angle in this image point. In image points with predominantly aqueous tissue, as mentioned above the signal intensity of the signal magnitude in this image point can be used to determine the initial variance. If the tissue in an image point for which an initial variance should be determined has been heated relative to the surrounding tissue, the phase change induced by the heating can also be taken into account in the determination of the variance. For example, the phase change induced by the heating can be used in order to determine a maximum phase change, and this can be used as a minimum standard deviation. If the heated region is known, for example, the highest temperature in the environment can be used (for example via a temperature model) in order to conclude a maximum temperature-induced phase change from the highest temperature.

In the second group of image points in which the variance should be determined with the aid of a model, image points which do not contain any reliable phase information can be contained for which a phase information and a variance should, however, be estimated via the linear transformation. Furthermore, this second group can contain image points for which no phase value should be estimated via the linear transformation. For image points outside of the body, or image points within vessels or implants, the phase value in the image point has no information that corresponds to a slow variation across the image plane. For example, for these image points it is advantageous to estimate no phase value and no variance and, in the case of the iteration, the variance of these image points between the iterations steps can in turn be set as "unknown" so that, in the linear transformation, the phase values in these image points do not affect the phase values in other image points in which a phase value should be estimated. For example, these image points can be set as "unknown" via a very high variance.

It is likewise possible to compare with one another phase image data sets that were estimated via different linear transformations. The phase image data sets generated with different linear transformations should respectively result after the iteration in the final phase image data set that reflects the system-dependent phase values in the image points. If the difference between two final image data sets is greater than a limit value that can result from the variances, an error message can be generated and indicated, for example. In one embodiment the MR system-dependent phase information determined as above can be used to calculate a temperature value in an image point that is determined with the aid of the phase values of the MR phase image data set.

For image points in which the initial variance is essentially calculated under consideration of the signal intensity of a background signal with the aid of the signal intensity in the associated image point, a Laplace approximation method can be applied to the complex MR signals in the calculation.

The invention likewise concerns an MR system with which the aforementioned method can be implemented. In particular, the MR system has a computer that implements the variance-dependent addition of the phase image data sets.

DESCRIPTION OF THE PREFERRED EMBODIMENTS

Figure 1:
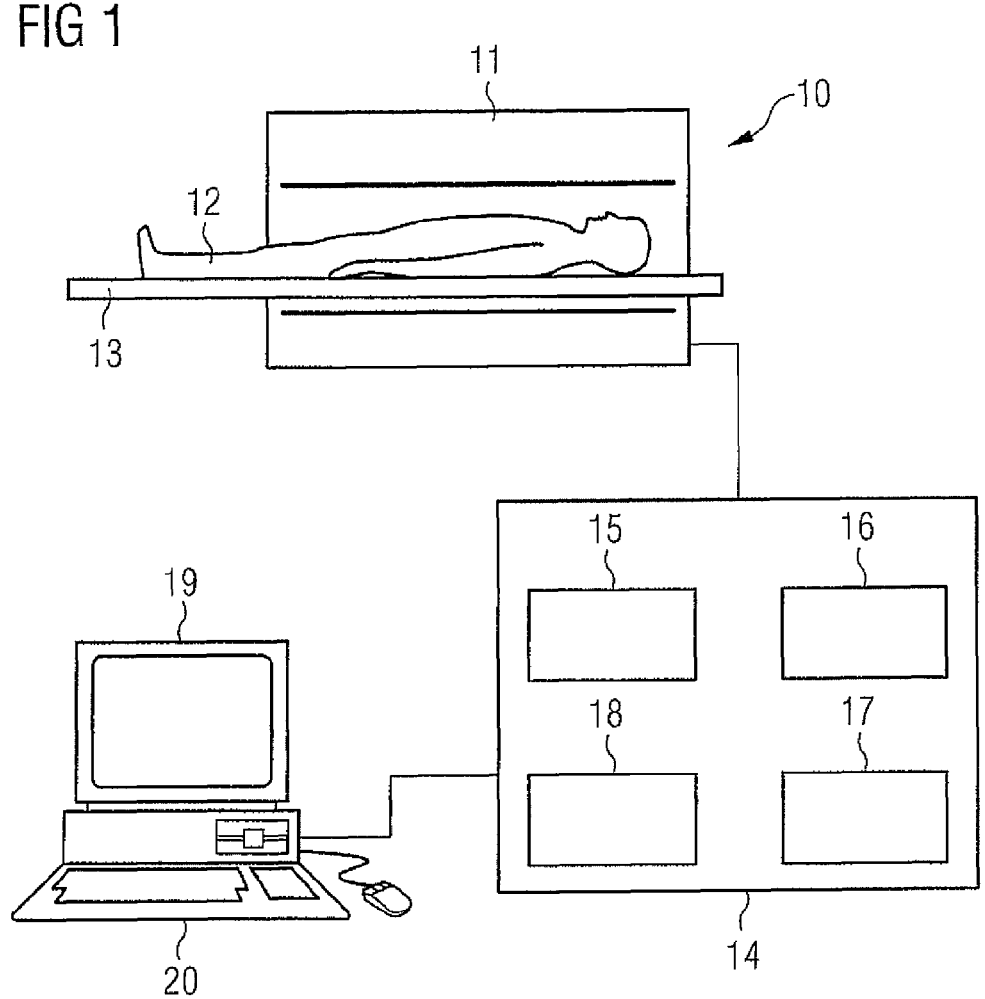
FIG. 1 schematically shows an MR system with which an MR system-dependent phase information can be calculated.

Shown in FIG. 1 is an MR system 10 with a magnet 11 to generate a B0 field into which can be inserted an examined person 12 who is arranged on a bed 13. For example, the shown MR system can be used for a thermotherapy in which individual regions of the body of the examined person are heated in order to destroy localized tumor tissue in the heated region. With acquisition of MR signals and the generation of phase images, the temperature development in the examined person can be checked non-invasively in two or three dimensions, for example in that gradient echo sequences with a predetermined echo time TE are used in order to conclude a temperature change $\Delta T$ in a phase change $\Delta\phi$. The MR system 10 has a central control unit 14 with which the MR system can be controlled. Only a few components of the MR system are described in the following, since how an MR image can be generated (via detection of the MR signal by radiation of RF pulses by an RF control unit 15 and simultaneous switching of gradient pulses by a gradient control unit 16) is known in general to the man skilled in the art. The sequence of the radiation of the RF pulses and the switching of the gradients is controlled in a sequence control unit 17. The MR intensity image or, respectively, MR phase image can then be calculated in a computer 18 and be presented on a display 19. An operator can control the selection and input of an imaging sequence via an input unit 20. Furthermore, the phase (which is dependent on the MR system or, respectively, the B0 instability) can be calculated in the computer 18.

In temperature imaging by means of the chemical shift, a temperature change $\Delta T$ is detected as a phase change $\Delta\pi$, wherein the following correlation exists between $\Delta\phi$ and $\Delta T$:

$$\Delta\phi = \gamma B_0 \alpha \Delta T \cdot TE \qquad (1)$$

wherein TE is the echo time of the imaging sequence, $\gamma$ is the gyromagnetic ratio, and B0 is the field strength and $\alpha$ is the temperature dependency of the chemical shift that amounts to $-0.01$ ppm/° C. However, the phase information resulting from the MR signal can also be of importance in other fields, for example in susceptibility-weighted MRT, in phase contrast MRT or in flow measurement by means of phase coding.

In all applications that are based on phase information, it is important to know the phase change (induced by a B0 instability, for example). Furthermore, it is important to known the phase development across the image that is induced independent of the selected imaging sequence and the echo time, for example due to the acquisition path or due to spatial B0 inhomogeneities.

Figure 2:
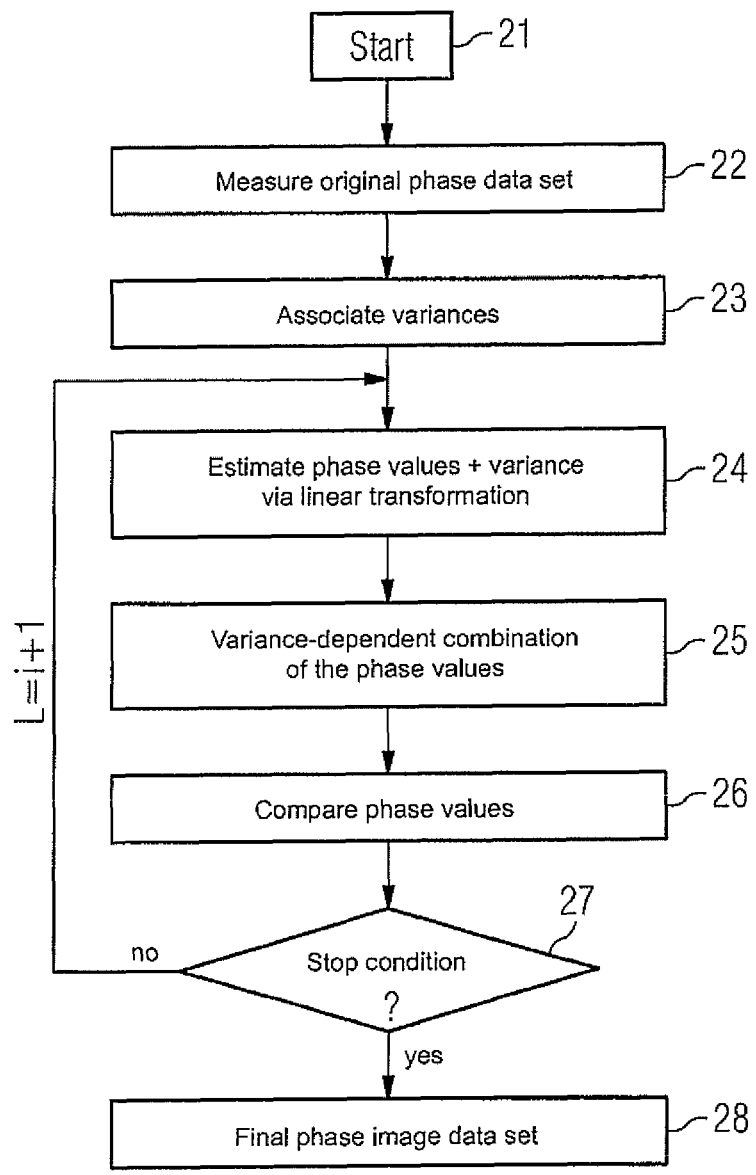
FIG. 2 is a flow chart for implementation of the calculation of the MR system-dependent phase information.

In FIG. 2 a method is shown with which the systems-dependent spatial phase distribution across the field of view of the MR system can be determined. After the start of the method in Step 21, in Step 22 original phase data are acquired, meaning that an MR data set is acquired and the phase of the detected MR signal is shown in each image point. In addition to the phase information, the magnitude information of the MR signal can also be determined by absolute value calculation of the imaginary part and real part of the acquired signal, as is known to those skilled in the art. When the original phase information in the individual image points is known, in Step 23 initial variances can be associated with the individual image points. The uncertainties in the original phase data and the uncertainties of a model that is set up or used for the determination of the variances in the individual image points are taken into account.

The phase image data set measured (acquired) in Step 22 contains image points with a relatively well defined uncertainty, and this original phase data set also contains image points at which prior information based on a model is used in order to determine the variances. For example, if the image points contain only portions of water and no fat, the variance in these image points can be determined depending on the magnitude of the signal in this image point. If the magnitude signal is rather high the variance is rather smaller, while the variance in an image point will be increased given a small signal contribution. Since the signal intensity changes from image point to image point, the variance also changes from image point to image point. For example, an initial variance for these image points can be calculated with the signal intensity of the MR magnitude signal and the signal intensity of the background signal. One embodiment is the application of the Laplace approximation method to the complex MR signals with consideration of the error propagation of Gaussian errors. The influence of an error in "x" is estimated at a variable "y" calculated from "x" via a (possibly multidimensional) Taylor representation. In the event that it is possible to suppress the fat signal in these image points or to calculate the proportion of the fat signal, this also applies for image points that contain fat. As is known, the fat/water proportion in an image point can be determined via the Dixon method. Image points that essentially contain fat can also be identified with the aid of segmentation algorithms in addition to the known Dixon method. Given image points that contain only fat, the system-dependent phase change cannot be separated from the phase change due to a temperature change, for example. However, since fat does not have any temperature-dependent phase change, a phase change in fat can be estimated with $\omega_{fat} \times T_n$. The average value and the variance of the system-induced phase read:

$$\text{Estimate}[\omega_{\Delta B0}] = \omega_{measured} - \text{Estimate}[\omega_{fat}]$$

$$\text{Variance}[\omega_{\Delta B0}] = \text{Variance}[\omega_{measured}] + \text{Variance}[\text{Estimate}[\omega_{fat}]] \quad (2)$$

$\omega_{measured}$ here is the measured frequency, $\omega_{\Delta B0}$ is the system-dependent frequency change, whereby the variance of the system-dependent frequency change results from the variance of the measured frequency and the variance of the estimated fat frequency.

If image points are present that essentially contain fat, the fat image points can be used as a temperature-independent reference phase so that it is possible to determine the system-dependent deviation of the resonance frequency. In the event that phases should be determined in body regions that are heated, the phase change induced by the heating can be taken into account in the determination of the initial variance according to the above Equation 1. However, for this it is necessary to have approximate information about the temperature change in the individual regions. Furthermore, in the original phase data set image points are identified for which no variance and no phase information should be determined based on a model, for example at image points that contain vessels or at image points at which the susceptibility differs significantly from that of the surrounding tissue. Although the variance value is unknown at tissues with slight susceptibility differences, it should be calculated as explained in the following via iteration and linear transformation. Given image points outside of the body or in vessels [or] implants, the phase information does not follow the presumed harmonic field development of a slightly changing field, such that here it is advantageous to not calculate the variance or, respectively, to assume the variance to be unknown again after each calculation in the iteration.

If the variances in the individual phase image points are associated, it is possible to estimate the phase values and the variance in Step 24 by a linear transformation. This linear transformation can be implemented via multiplication of the original phase data set with a filer kernel. An example of a filter kernel can be:

$$F = \begin{pmatrix} 0 & 0,25 & 0 \\ 0,25 & 0 & 0,25 \\ 0 & 0,25 & 0 \end{pmatrix}$$

Naturally, other filter kernels (Gaussian filter kernels, for example) can also be used. A filter kernel with weightings w can be applied to a phase data set $s^{i-1}$ with the original phase data being replaced by the weighted sum of w and x and $s^{i-1}$, wherein the x corresponds to an aliasing. The index i corresponds to the iteration step during the iteration, as is explained in detail in the following. In order to account for the original data, a binary mask m and an inverse mask $\overline{m}$ are used. By transformation of the data, the aliasing can be represented as a multiplication, such that the following applies:

$$s^i = m s^{i-1} + \overline{m} w \otimes s^{i-1} \Rightarrow I^i = M I^{i-1} + \overline{M} W I^{i-1} \quad (3)$$

According to the invention, instead of 0 and 1 for the values of m or, respectively, $\overline{m}$, each value is now accounted for depending on the variance of each value according to following Equation:

$$s^i = ((v^0)^{-1} + (v_{ws}^i)^{-1})^{-1}((v^0)^{-1} s^0 + (v_{ws}^i)^{-1} w \otimes s^{i-1}) \Rightarrow$$
$$I^i ((V^0)^{-1} + (V_{WI}^i)^{-1})^{-1}((V^0)^{-1} I^0 + (V_{WI}^i)^{-1} W I^{i-1}) \quad (4)$$

wherein $s^0$ and $v^0$ are the original phase information and the variance associated with this, $s^{i-1}$ is the phase information of the preceding iteration and $v_{ws}^i$ is the variance of the data aliased with the kernel. After the preceding transformation, the above Equation 4 results with corresponding variables $I^0$, $V^0$, $V^{i-1}$ and $V_{wi}^i$. As is apparent from the above Equation 4, the initial phase value is weighted with the initial variance. The term in the first large bracket with $V^0$ and $V_{wi}^1$ serves for normalization. The variable $I^0$ corresponds to the phase information in the image with the originally associated initial variance $V^0$, and $V_{wi}^i$ is the variance of the data aliased with the kernel. It is now necessary to determine the variable $V_{wi}^i$. This variable represents the variance of $WI^{i-1}$ and can easily be calculated. If a discrete, linear transformation of a vector x is represented as a matrix M, the result vector y can be calculated via the formula $y = M \cdot x$. If x is subject to a Gaussian error statistic (with average=0 and covariance matrix Cx), the covariance matrix of the result Cy is then given by the formula $Cy = M \cdot Cx \cdot M^t$. Here the function $^t$ stands for complex transposition. The principal diagonal of this covariance matrix contains the variances of the values y. The variance of $I^{i-1}$ can now be calculated since this is also provided by a linear transformation (Equation (4)).

In a next step the phase values can now be combined depending on the variance, i.e. the original phase values of Step 22 with the estimated phase values of Step 24 (Step 25). If the variance of a phase value is small, its weighting in the addition of the phase values will be high; if the variance is large, the weighting will be small, since this suggests a large uncertainty in the determined phase values. By the application of the filter kernel, the phase contained in an image point is transferred to the other adjacent image points, and a new, additional phase image data set results. This new phase image data set can be compared with the original phase image data set (Step 26). If the difference between the newly created phase image data set and the original phase data set is greater than a predetermined limit value, this means that the stop condition checked in Step 27 is not yet satisfied and the application of the filter kernel to the new data—i.e. the estimation of the phase values and the variance via the linear transformation—is repeated. In Step 26 the phase image data sets of the iteration steps i and i−1 are then compared again, and the linear transformation is repeated until the difference in the phase image data sets is smaller than the predetermined limit value in successive iterations, which forms a stop condition for the iteration. If the stop condition is satisfied, this means that the final phase image data set exists in Step 28, which then corresponds to the phase information that is due to the MR system and the acquisition path.

If it is not clear which filter kernel should be used for the linear transformation in Step 24, multiple filter kernels $w^P$ or $W^P$ can also be used and the results can be weighted depending on the variances. For example, the filter kernel can be an interpolating or extrapolating kernel. For multiple filter kernels P, the above Equation 4 can be generalized as follows.

$$s^i = \left((v^0)^{-1} + \sum_{p=1}^{P}(v^{ip}_{ws})^{-1}\right)^{-1}\left((v^0)^{-1}s^0 + \sum_{p=1}^{P}(v^{ip}_{ws})^{-1}\sum_{p=1}^{P}w^p \otimes s^{i-1}\right) \quad (5)$$

$$\Rightarrow I^i = \left((V^0)^{-1} + \sum_{p=1}^{P}(V^{ip}_{WI})^{-1}\right)^{-1}\left((V^0)^{-1}I^0 + \sum_{p=1}^{P}(V^{ip}_{WI})^{-1}W^p I^{i-1}\right)$$

As in Equation 4, this formulation ignores the fact that the errors in the variances may be correlated. Furthermore, here it can be advantageous to take into account special or experiment-based weightings $k^p$. For example, this can take place in order to place more weight on interpolating filter kernels, for example if data from a closed surface or a closed contour around the image points of interest are used instead of extrapolating filter kernels. Furthermore, the weightings can be used in order to reduce the proportion of the data calculated via the kernel in comparison to the original data. Otherwise the data aliased with the kernel would dominate the original data; it is hereby possible to set $$w^p = \frac{1}{p},$$

from which Equation 6 follows.

$$s^i = \quad (6)$$

$$\left((v^0)^{-1} + \sum_{p=1}^{P}\kappa^p(v^{ip}_{ws})^{-1}\right)^{-1}\left((v^0)^{-1}s^0 + \sum_{p=1}^{P}\kappa^p(v^{ip}_{ws})^{-1}\sum_{p=1}^{P}w^p \otimes s^{i-1}\right)$$

$$\Rightarrow I^i = \left((V^0)^{-1} + \sum_{p=1}^{P}\kappa^p(V^{ip}_{WI})^{-1}\right)^{-1}\left((V^0)^{-1}I^0 + \sum_{p=1}^{P}\kappa^p(V^{ip}_{WI})^{-1}W^p I^{i-1}\right)$$

The variance in an iteration step i is then $$V^i = \text{Variance}(I^i) = \left((V^0)^{-1} + \sum_{p=1}^{P}\kappa^p(V^{ip}_{WI})^{-1}\right)^{-1} \quad (7)$$

Since each phase image data set filtered with the filter kernel should ultimately lead to an identical (namely the final) phase image data set, a per-pair addition of data sets can be used in order to test the calculation for inconsistencies. In general, the difference between two calculated phase image data sets should be smaller than the standard deviation of the sum.

$$x=(v_1+v_2)^{-1/2}(s_1+s_2) \Rightarrow X=(V_1+V_2)^{-1/2}(S_1-S_2) \quad (8)$$

X is thus the distance in standard deviations between the data points. If this value is large, the underlying model is incorrect and the calculation of the final phase image data set can, for example, be terminated, or an operator can be informed. As an alternative to this, the probability that two phase data sets have a defined distance can be calculated as follows:

$$P(s_1 - s_2 \mid v_1, v_2) = \quad (9)$$

$$(2\pi)^{-1}\text{Det}(v_1 + v_2)^{-1}\text{Exp}\left(-\frac{1}{2}(s_1 - s_2)^*(v_1 + v_2)^{-1}(s_1 - s_2)\right)$$

$$\Rightarrow P(I_1 - I_2 \mid V_1, V_2) =$$

$$(2\pi)^{-1}\text{Det}(V_1 + V_2)^{-1}\text{Exp}\left(-\frac{1}{2}(I_1 - I_2)^*(V_1 + V_2)^{-1}(I_1 - I_2)\right)$$

This probability can be used to identify the image points in which artifacts dominate the phase information, or image points in which the proposed model does not function.

In summary, the method described in the preceding has the advantage that more image points can be used in the estimation of the MR system-dependent phase information, wherein each image point is weighted depending on the composition and the signal-to-noise ratio. Furthermore, the variances can be observed over the different iterations, and different filter kernels can be combined.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to determine magnetic resonance (MR) system-dependent phase information of a phase value in an MR phase image data set, comprising the steps of:
   providing a first MR phase image data set to a processor that was acquired by operation of an MR system, said first MR phase image data set representing a plurality of image points;
   in said processor, associating initial variances with respective image points of said first phase image data set;
   for calculating an additional phase image data set, estimating, in said processor, a phase value and a phase variance of the phase value for respective image points of said second phase image data set by a linear transformation of said image points of said first phase image data set; and
   in said processor, calculating said second phase image data set by a weighted addition of the phase values of the first phase image data set with the estimated phase values, said weighting being dependent on the estimated variance of the phase value.

2. A method as claimed in claim 1 comprising, in said processor, for each image point, the higher the variance of the phase value, the lower the weighting of that phase value in said addition.

3. A method as claimed in claim 1 comprising associating said initial variances with said image points of said first phase image data set to produce a first group of image points of said first phase image data set at which said variance substantially depends on a signal-to-noise ratio of an MR signal produced by said MR system, and a second group of image points of said first phase image data set for which the variance is determined using a model based on the image points.

4. A method as claimed in claim 1 comprising iteratively calculating said second phase image data set with a variance-dependent addition of the phase values in an iteration step i−1 with the phase values of a phase image data set calculated in an iteration step i, up to calculation of a final phase image data set in which a difference between the phase values in a last two iteration steps is smaller than a predetermined limit value, said final phase image data set corresponding to said MR system-dependent phase information.

5. A method as claimed in claim 1 comprising implementing said linear transformation by aliasing said first phase image data set with a filter kernel.

6. A method as claimed in claim 5 comprising estimating said second phase image data set by aliasing with multiple, different filter kernels and associated variances with phase values resulting from the aliasing with the filter kernels being respectively weighted dependent on the associated variance.

7. A method as claimed in claim 1 comprising determining said initial variance for an image point in which fat tissue predominantly contributes to an MR signal acquired with said MR system to produce said first MR phase image data set, by determining a fat-induced phase angle and a measured phase angle for said image point.

8. A method as claimed in claim 1 comprising determining the initial variance for an image point in which aqueous tissue predominantly contributes to an MR signal acquired by said MR system to produce said first MR phase image data set, based on a signal intensity of a magnitude of said MR signal.

9. A method as claimed in claim 1 comprising determining said initial variance dependent on a temperature-induced phase change for an image point representing tissue that was heated relative to surrounding tissue.

10. A method as claimed in claim 1 comprising associating said initial variances with said image points of said first phase image data set to produce a first group of image points of said first phase image data set at which said variance substantially depends on a signal-to-noise ratio of an MR signal produced by said MR system, and a second group of image points of said first phase image data set for which the variance is determined using a model based on the image points and wherein said second group comprises image points containing no reliable phase information, said image points of said second group comprising image points for which a phase value is to be estimated by said linear transformation, and image points for which no phase value is to be estimated by said linear transformation.

11. A method as claimed in claim 1 comprising comparing phase image data sets estimated with different linear transformations to each other, and generating, and making humanly perceptible, an error message if a difference between two estimated phase image data sets is greater than a predetermined limit value.

12. A method as claimed in claim 1 comprising using said MR system-dependent phase information to calculate a temperature value from the phase values of the MR phase image data set.

13. A method as claimed in claim 1 comprising calculating said initial variance using a signal intensity of an MR magnitude signal and a signal intensity of a background signal acquired by said MR system, using a Laplace approximation to the complex MR signals.

14. A magnetic resonance apparatus comprising:
a magnetic resonance data acquisition unit configured to acquire a first phase image data set comprising a plurality of image points; and
a processor provided with a first MR phase image data set that was acquired by operation of an MR system, said first MR phase image data set representing a plurality of image points, said processor being configured to associate initial variances with respective image points of said first phase image data set and to calculate an additional phase image data set, and configured to estimate a phase value and a phase variance of the phase value for respective image points of said second phase image data set by a linear transformation of said image points of said first phase image data set, and configured to calculate said second phase image data set by a weighted addition of the phase values of the first phase image data set with the estimated phase values, said weighting being dependent on the estimated variance of the phase value.

* * * * *